United States Patent [19]

Lampotang et al.

[11] Patent Number: 4,928,687
[45] Date of Patent: May 29, 1990

[54] CO2 DIAGNOSTIC MONITOR

[75] Inventors: Samsun Lampotang; Dietrich Gravenstein; Joachim S. Gravenstein; Nikolaus Gravenstein; Michael J. Banner, all of Gainesville, Fla.

[73] Assignee: The University of Florida, Gainesville, Fla.

[21] Appl. No.: 255,400

[22] Filed: Oct. 11, 1988

[51] Int. Cl.⁵ .............................................. A61M 16/00
[52] U.S. Cl. ................ 128/207.14; 128/205.23; 128/200.26
[58] Field of Search ................... 128/207.14, 716, 719, 128/204.22, 205.23, 200.26; 436/133; 422/86

[56] References Cited

U.S. PATENT DOCUMENTS

| | | |
|---|---|---|
| 2,136,236 | 11/1938 | Draper . |
| 2,638,096 | 5/1953 | Waldhaus . |
| 2,890,177 | 6/1959 | Kilmer ................................. 436/133 |
| 3,114,610 | 12/1963 | Gafford et al. ...................... 436/133 |
| 3,507,623 | 4/1970 | McConnaughey ................... 422/86 |
| 4,155,358 | 5/1979 | McAllister . |
| 4,326,515 | 4/1982 | Shaffer et al. .................. 128/207.17 |
| 4,428,907 | 1/1984 | Heijenga .............................. 422/86 |
| 4,538,606 | 9/1985 | Whited ........................... 128/207.15 |
| 4,607,643 | 8/1986 | Bell et al. .......................... 128/715 |
| 4,632,119 | 12/1986 | Reichstein ........................... 128/632 |
| 4,691,701 | 9/1987 | Williams ......................... 128/207.14 |
| 4,728,499 | 3/1988 | Fehder ................................. 422/56 |
| 4,740,475 | 4/1988 | Paul ..................................... 422/86 |

Primary Examiner—Edgar S. Burr
Assistant Examiner—Aaron J. Lewis
Attorney, Agent, or Firm—Kerkam, Stowell, Kondracki & Clarke

[57] ABSTRACT

A diagnostic monitor checks the carbon dioxide ($CO_2$) content of a gas exiting a patient during endotracheal or esophageal intubation. A plurality of composition portions substantially change color in response to exposure to the carbon dioxide. The composition portions change color in response to different times of exposure to carbon dioxide. A magnifying or condensing lens may be positioned on the monitor to enhance viewing of the color change. The monitor may advantageously be made as part of an intubation system through which the gases from a patient exit the patient. The differences in time of exposure needed to cause the color change may be accomplished by using semipermeable membranes having differing thicknesses, $CO_2$ permeabilities, and/or surface areas with each membrane corresponding to a particular one of the composition portions.

30 Claims, 8 Drawing Sheets

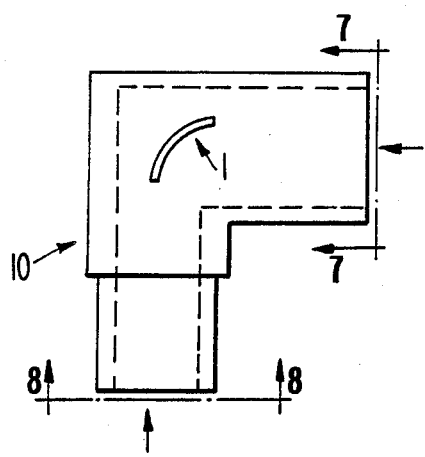
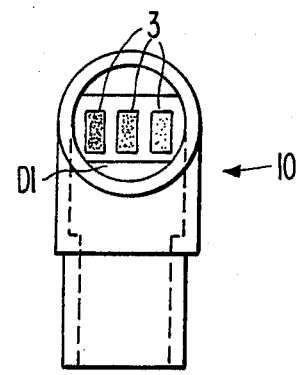
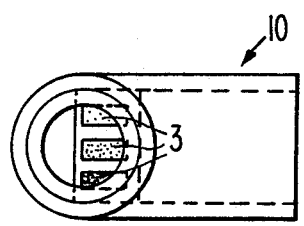
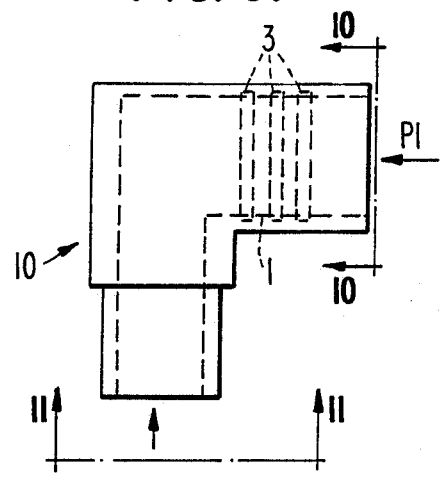
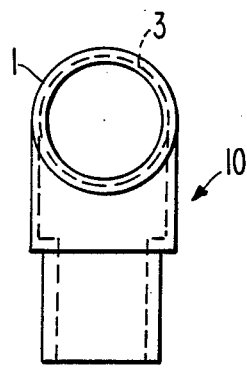
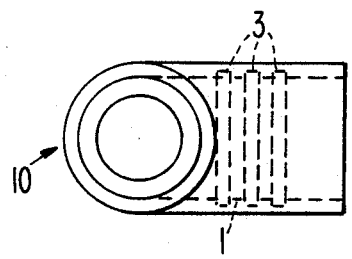

INDICATOR SATURATED GAUZE MATRIX 3

INDICATOR SATURATED GAUZE MATRIX 3

CO₂ DIAGNOSTIC MONITOR

BACKGROUND OF THE INVENTION

1. Field of the Invention

The present invention relates to monitoring $CO_2$ during endotracheal and esophageal intubations.

2. Description of the Prior Art

The physical proximity of the esophageal opening to the tracheal opening makes accidental esophageal, instead of tracheal, intubation an unfortunately common occurrence. If the esophageal intubation goes undetected the patient may be deprived of oxygen, possibly leading to morbidity or mortality. Moreover, tracheal intubation can occur accidentally in procedures where esophageal intubation was intended.

A recent study of 624 closed malpractice claims found esophageal intubation to be the most frequent specific critical incident during endotracheal intubation involving anesthesiology: 41 cases of esophageal intubation, 8 causing brain damage and 31 ending in death [Cheney, Butterworths, Boston, 1988, Gravenstein and Holzer (Eds.)] A study by Keenan and Boyan of 27 cardiac arrests due to anesthesia showed 4 incidences of unrecognized esophageal intubation [Journal of American Medical Association, Vol. 253, No. 16, pp. 2373-2377 (1985)]. Cooper et al found 18 cases of esophageal intubation out of 507 "critical incidents" and 3 out of 70 anesthesia cases with "substantive negative outcome" [Anesthesiology, Vol. 60, pp. 34-42 (1984)]. In a study of emergency intubation in the field by paramedical personnel, Stewart et al noted 14 cases of esophageal intubation out of 74 reported complications [Chest, Vol. 85:3, pp. 341-5 (1984)].

Many prior art attempts to detect either endotracheal or esophageal intubation where the other procedure was intended are based on the fact that the stomach liberates practically no carbon dioxide whereas the lungs liberate prodigious amounts of $CO_2$ (200 mL/min for an adult).

These previous attempts can be summarized as follows:

End-Tidal Carbon Dioxide Measurement

This method is the industry standard for early detection of esophageal intubation [Murray et al, Anesthesiology, Vol. 59, pp. 344-346 (1983)]. It includes (a) capnometry, the measurement of carbon dioxide concentration (by absorption of infra-red light) during the respiratory cycle, (b) capnography, the display of measured carbon dioxide concentration as a waveform and (c) mass spectrometry which can produce both a $CO_2$ waveform and a digital value. With the above methods, absence of $CO_2$ in the exhaled breath is a reliable indication of esophageal intubation [Birmingham et al, Anesth. Analg., Vol. 65, pp. 886-891 (1986)].

These systems suffer from numerous disadvantages: high costs (apnea monitors, capnographs, and mass spectrometers are expensive and not affordable by smaller hospitals); bulky (additional components require the utilization of space needed for other systems); power requirements (the additional components require electrical power to operate which is not always available); additional tasks by medical personnel (the additional components require the operator to divide his time between performing critical services and operating and monitoring these complicated systems); warm-up time (capnographs require a long warm-up time which prevents an early detection of presence or absence of $CO_2$).

Einstein Carbon Dioxide Detector

This system detects carbon dioxide by bubbling one exhalation through 6 mL of a chemical indicator consisting of 50% cresol red and 50% phenolphthalein (stock solutions), placed in a clear container. The method consists of inflating the lungs after intubation, occluding the endotracheal tube at the proxixmal end with a hemostat to prevent escape of expired gas, connecting the device to the endotracheal tube and then releasing the hemostat to allow the expired breath to bubble through the indicator. Presence of carbon dioxide in the exhaled breath causes a color change from red to yellow within 3-5 seconds [Berman et al, Anesthesiology, Vol. 60, pp. 613-614 (1984)].

The large number of additional actions that the Einstein $CO_2$ indicator requires of the operator makes it an impractical solution.

Six mL of chemicals so close to the airway may find their way into the lung, for example, if the patient spontaneously inhales when connected to the device. There is always the risk that the solution might be spilled, rendering the device useless and possibly contaminating a sterile field.

Since only the first exhalation after intubation is checked, the probability of false positives is increased. For example, a patient who has just had CPR might conceivably have some $CO_2$ from the rescuer's breath in the stomach; or the patient might just have drunk a carbonated drink or had face mask ventilation with rebreathing so that there is some $CO_2$ in the stomach. For those cases, the Einstein indicator will give a false positive in the event of esophageal intubation because the $CO_2$ in the stomach will trigger the indicator and fool the operator.

CO₂ Detector

In the 1950's, there was concern about the effectiveness of $CO_2$ absorbers and $CO_2$ detectors were placed in the inhalation limb of circle systems to measure rebreathed $CO_2$ concentration. Scrubbed gas was drawn into a calibrated bulb and then forced in the form of fine bubbles through a solution of calcium or barium hydroxide containing an indicator. The concentration of $CO_2$ was determined by the number of squeezes of the calibrated bulb required to obtain a color change of the indicator solution [Hugin, Benno Schwabe Verlag., Basel, pp. 100-101 (1951); Adriani, The Chemistry and Physics of Anesthesia, Thomas, Springfield, pp. 179-180 (1962)]. If placed in the exhalation limb of the circle system, these $CO_2$ detectors will determine the $CO_2$ concentration in the exhaled breath and thus alert the user to esophageal intubation. However, the additional equipment to be added to the circuit rendered the technique unwieldy and required additional actions by the operator.

Lighted Stylet

This technique utilizes the opacity of the muscle around the esophagus to indicate where the endotracheal tube is situated. Since the trachea is anterior to the esophagus, a high intensity light bulb at the tip of a stylet placed in the endotracheal tube will transilluminate the soft tissues in the neck. If the endotracheal tube is in the esophagus, the muscle around the esophagus will attenuate the intensity of the light [Yamamura et al, Anesthesiology, Vol. 20, pp. 221–222 (1959); Foster, Anaesthesia, Vol. 32, pp. 1038 (1977); Ducrow, Anaesthesia, Vol. 33, pp. 827–829 (1978); Vollmer et al, Annals of Emergency Medicine, Vol. 14:4, pp. 324–328 (1985); Ellis et al, Annals of Emergency Medicine, Vol. 15:2, pp. 138–142 (1986); Ellis et al, Anesthesiology, Vol. 64, pp. 823–826 (1986).

The lighted stylet, however, does not work well in bright, direct light and does not work well with obese people. The device depends on batteries which may become inoperable at critical times. The presence of the hot filament in the light bulb may also be an undesirable feature in the presence of an enriched oxygen atmosphere. The lighted stylet also obstructs the endotracheal tube during use and represents a possible source of tissue burns.

Chest Radiography

An X-ray of the chest can be used to verify proper tube placement [Birmingham, supra]. Chest radiography is time consuming and expensive. Chest radiography requires skillful interpretation and even then may not be fail-safe [Batra et al, Critical Care Medicine, Vol. 11, pp. 763–764 (1983)]. Moreover, chest radiography requires a lateral view for confirmation and is often not available in the field and in a hospital, it may not be available on short notice.

Fiberoptic Bronchoscopy

This instrument allows viewing of the tracheal rings and the carina, if the endotracheal tube is in the trachea. It is a reliable method of verifying tube placement [Birmingham, supra]; however, it is quite expensive and is prone to breakage. Moreover, the method is unwieldy for routine use and use in the field and it requires a skilled operator.

Pulse Oximetry

A pulse oximeter measures the oxygen saturation of arterial blood ($SaO_2$) and is a late indicator of esophageal intubation. Apart from the time that it normally takes for compromised ventilation to show up as a drop in $SaO_2$, three other factors also tend to delay the onset of hypoxia in the event of esophageal intubation: (a) the common practice in anesthesia of preoxygenation before intubation [Howells et al, Anaesthesia, Vol. 35, pp. 984–986 (1980); Howells, Anaesthesia, Vol. 40, p. 86 (1985); Howells, Anaesthesia, Vol. 40, p. 387 (1985)], (b) indirect lung ventilation through compression by the stomach provides a certain amount of oxygenation [Linko et al, Acta Anaesthesiol. Scand., Vol. 27, pp. 199–202 (1983)] and (c) a non-paralyzed patient may be able to breathe and maintain $SaO_2$ at elevated levels.

Pulse oximetry is a slow detector of esophageal intubation. Precious minutes may elapse before the esophageal intubation is detected and surgery may even have already started, an undesirable situation with possibly catastrophic consequences. Even if a low oxygen saturation, indicative of hypoxia is measured, the cause might be something other than esophageal intubation, e.g., decreased inspired oxygen concentration ($FIO_2$) with tracheal intubation, atelectasis or wrong gas mixture.

Eschmann Endotracheal Tube Introducer

The introducer is a narrow, 60 cm long, fiberglass stylet that is inserted in the lumen of an endotracheal tube. If the tube is in the esophagus, the introducer will pass unopposed to the distal esophagus or stomach whereas if it is in the trachea, the tip will make contact with the carina or the cartilage of a main stem bronchus at 28–32 cm [Birmingham, supra].

The maneuver required is too cumbersome for routine use and the introducer in the hands of an overzealous and unskilled operator could conceivably puncture a bronchus, the esophagus or the stomach.

Video Stethoscope

In this system, the output from two microphones, one on each hemithorax, is displayed in an X-Y format on an oscilloscope. Distinct patterns are associated with tracheal intubation and esophageal intubation, allowing easy detection [Huang et al, Anesth. Analg., Vol. 62, pp. 586–589 (1983)]. The video stethoscope is, however, awkward to use and the technique is time-consuming.

The preceding methods and systems depend on equipment of one sort or another to detect esophageal intubation. For the sake of completeness, several non-equipment related techiques for detecting esophageal intubation are briefly described below, it being understood that this is not an exhaustive list of such techniques. In general, these latter techniques depend heavily on the senses, skill and experience of the operator. Such reliance on the sometimes imperfect human senses causes the diagnosis to be subjective and unreliable. These techniques are more fully described by Birmingham, supra.

Direct Visualization

A reliable sign of tracheal intubation is the ability to directly see the vocal cords and the ET tube as it passes into the trachea. In some patients with cancer, burns or deformities, direct visualization of the vocal cords is impossible, even with the most experienced operator. Moreover, prior to, or during securing of the endotracheal tube to the patient, the tube might slip out of the trachea and into the esophagus or pharynx.

Breath Sounds

Even highly-trained, skilled and experienced practitioners are sometimes unable to detect esophageal intubation by auscultating the chest with a stethoscope. The presence of breath sounds is taken as an indication of tracheal intubation.

A trained ear is required and even then may very often be fooled since, during esophageal intubation, sound may be transmitted from the stomach to the lungs [Cheney, supra; Birmingham, supra]. In noisy environments, such as the interior of a helicopter ambulance, detection of esophageal intubation by auscultation would be even more difficult, if not impossible. In addition, if the patient has an intrathoracic stomach, breath sounds will be heard with esophageal intubation [Howells (1980) supra; Heiselman, supra].

Epigastric Auscultation and Observation

The sound of air movement in the stomach during auscultation of the epigastrium is taken as a sign of esophageal intubation. The abdomen is observed for gastric distension, a possible sign of esophageal intubation; however, this method is not foolproof, especially with thinner or smaller individuals. Gastric distension might also be the consequence of mask ventilation prior to intubation.

Chest Movement

Symmetric bilateral movement of the chest wall during ventilation is used as an indication that the endotracheal tube is in the trachea; however, chest movement is difficult to evaluate in patients with large breasts, obesity or a barrel chest. Chest movement typical of lung ventilation can also sometimes be observed during esophageal intubation [Linko et al, supra]. Chest movement will also occur during esophageal ventilation of a patient with an intrathoracic stomach caused, for example, by a hiatal hernia [Ellis et al, supra; Howells, (1985) 40:387, supra].

It is an object of the present invention to provide an efficient, inexpensive and facile $CO_2$ monitor for use in endotracheal and esophageal intubation systems and methods which does not suffer from the disadvantages associated with the prior art devices.

SUMMARY OF THE INVENTION

These and other objects are realized by the present invention which provides a self-contained diagnostic monitor for screening the $CO_2$ content of a gas exiting a patient during endotracheal or esophageal intubation comprising: (1) a reservoir containing at least one composition having an initial pH in solution above about 3.8 and which substantially changes color in solution in response to exposure to $CO_2$, the reservoir having an opening adapted for communication only with the gas exiting and entering the patient during endotracheal or esophageal intubation; and (2) a semipermeable membrane which is permeable to $CO_2$, the membrane separating the at least one composition from the exiting and entering gases.

A further embodiment of the invention comprises an improved endotracheal or esophageal intubation system containing means through which gases exit the patient during the intubation; the improvement comprising a self-contained diagnostic monitor for screening the $CO_2$ content of a gas exiting the patient during the intubation comprising: (1) a reservoir containing at least one composition having an initial pH in solution above about 3.8 and which substantially changes color in solution in response to exposure to $CO_2$, the reservoir having an opening adapted for communication only with the gases exiting and entering the patient during the intubation; and (2) a semipermeable membrane which is permeable to $CO_2$, the membrane separating the at least one composition from the exiting and entering gas.

An additional embodiment of the invention comprises an improved method for monitoring the $CO_2$ content of gases exiting a patient during endotracheal or esophageal intubation, the improvement comprising contacting the exiting gases with a self-contained $CO_2$ diagnostic monitor comprising: (1) a reservoir containing at least one composition having an initial pH in solution above about 3.8 and which substantially changes color in solution in response to exposure to $CO_2$, the reservoir having an opening adapted for communication only with the exiting and entering gases during the intubation; and (2) a semipermeable membrane which is permeable to $CO_2$, the membrane separating the at least one composition from the exiting and entering gases.

BRIEF DESCRIPTION OF THE DRAWINGS

The invention may be more fully understood by reference to the following detailed description of specific embodiments, together with the accompanying drawings in which:

FIGS. 3, 6, 9 and 13 are side elevational views of an elbow joint connector tube containing a monitor of the invention in an endotracheal intubation system.

FIGS. 4, 7, 10 and 14 are views taken along lines 4—4, 7—7, 10—10 and 14—14, respectively, of FIGS. 3, 6, 9 and 13.

FIGS. 5, 8, 11 and 15 are views taken along lines 5—5, 8—8, 11—11 and 15—15, respectively, of FIGS. 3, 6, 9 and 13.

The present invention enables the detection of the occurrence of esophageal intubation, within the first delivered breaths after intubation, by exploiting the fact that the stomach liberates practically no carbon dioxide ($CO_2$) whereas the lungs liberate prodigious amounts of $CO_2$ (200 mL/min for an adult). There are many chemical indicators which change colors when exposed to $CO_2$. The appropriate indicators can thus be placed on the inexpensive, disposable monitor adapter of the present invention and mounted, for example, on the endotracheal (ET) tube. If the indicators do not turn color after intubation (absence of $CO_2$), the probability of an esophageal intubation is very high. Conversely, if the indicators do change color after intubation, there is a very high probability of tracheal intubation.

The systems and method of the invention are intended for use with both adults and infants in the surgical operating room, in ambulances and in the field, wherever intubation is required.

DETAILED DESCRIPTION OF THE SPECIFIC EMBODIMENTS

The invention is illustrated by the accompanying drawings wherein like numerals indicate like elevants.

Figure 1:
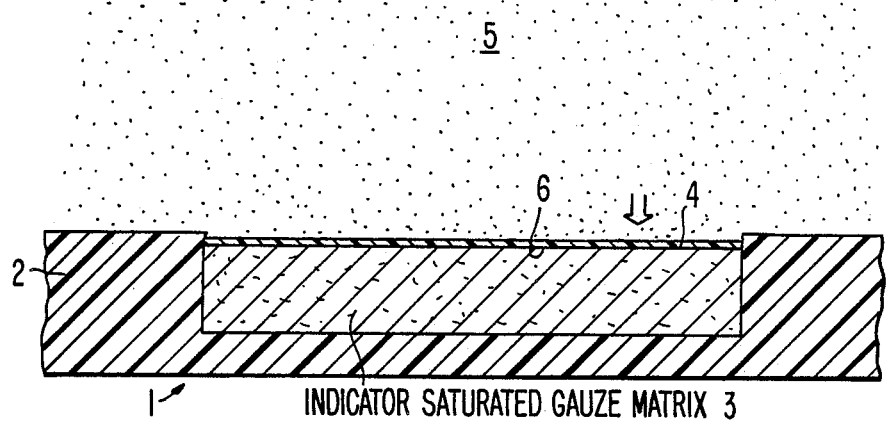
FIGS. 1 and 2 are side cross-sectional, cut-away views of the $CO_2$ monitor of the invention.
Figure 2:
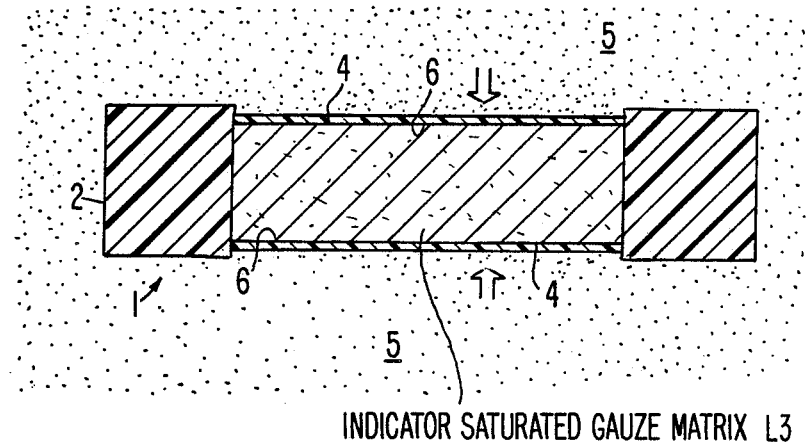

In FIGS. 1 and 2 the $CO_2$ monitor 1 comprises a reservoir 2, typically constructed of a plastic material similar to that employed in the construction of the endotracheal or esophageal tubes, preferably transparent; containing indicator gauze matrix 3 saturated with the indicator composition. Opening 4 is provided in the reservoir of FIG. 1 for communication with the gas atmosphere 5 entering or exiting the patient (not shown). In the embodiment shown in FIG. 2, two openings 4 are provided in the reservoir. A $CO_2$ permeable membrane 6 completely covers the hole(s) 4, thus separating the indicator composition 3 from the gas atmosphere 5. The arrows indicate the flow of gas through the membrane(s) 6 to the indicator composition 3.

Figure 3:
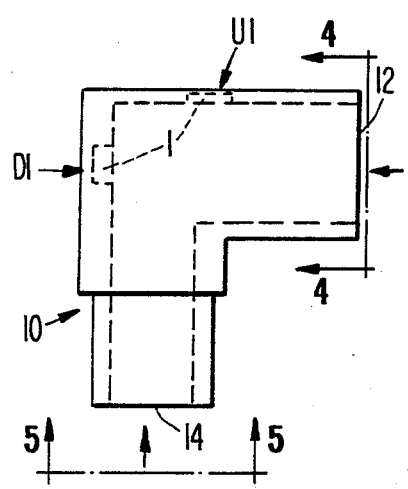

Referring to FIG. 3, the monitor 1 of FIG. 1 may be installed at either or both of areas U1 or D1 of a standard elbow joint connector tube 10 typically interposed between a conventional endotracheal tube (not shown) and conventional circle breathing or anesthesia breathing circuits (not shown). Gas flows (exhaled and fresh) are depicted by the labeled dark arrows at openings 12 and 14, respectively. U1 of the elbow tube indicates that area of the tube where a boundary layer of gas forms during the exhale cycle while D1 indicates that area of the tube wherein exhaled gas impinges directly on the wall of the tube thereby preventing the formation of a boundary layer at that area of the tube.

Figure 4:
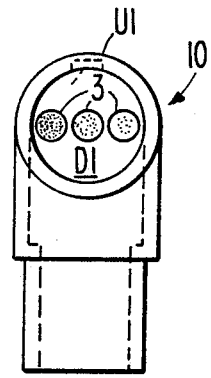

In FIG. 4, three indicator compositions 3 having different sensitivities represented by the varying degrees of shading are visible through the single membrane at area D1 of tube 10. Monitor 1 may also be positioned at area U1 of tube 10.

Figure 5:
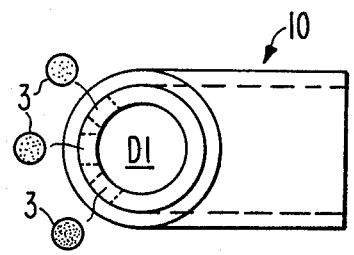

In FIG. 5, each of the indicator compositions 3 is shown in cross-section at area D1 of tube 10.

The two membrane monitor 1 of FIG. 2 may be installed in tube 10 as shown in FIG. 6 where it is depicted in an arcuate form and positioned so as to be exposed from both sides to gas from the patient, and such that the exhaled gas impinges directly on one side of the membrane.

FIGS. 7 and 8 depict views of the system of FIG. 6 from the two ends of the tube 10.

In FIG. 9, the monitor 1 consists of a cylindrical reservoir surrounding the tube 10 such that the indicator compositions 3 are exposed to gas flow around the entire inner circumference of the tube 10.

FIGS. 10 and 11 depict views of the system of FIG. 9 from the two ends of the tube 10.

Figure 12:
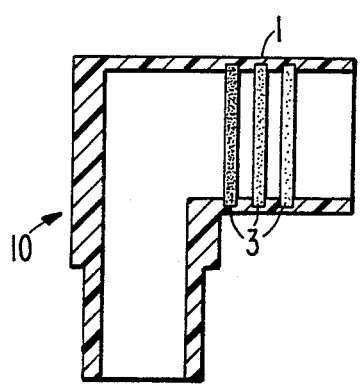
FIGS. 12 and 16 are cross-sectional views of FIGS. 9 and 13, respectively.

FIG. 12 is a cross-sectional, cut-away, view of the system of FIG. 9 showing the three indicator compositions of varying degrees of sensitivity by different shadings.

Figure 13:
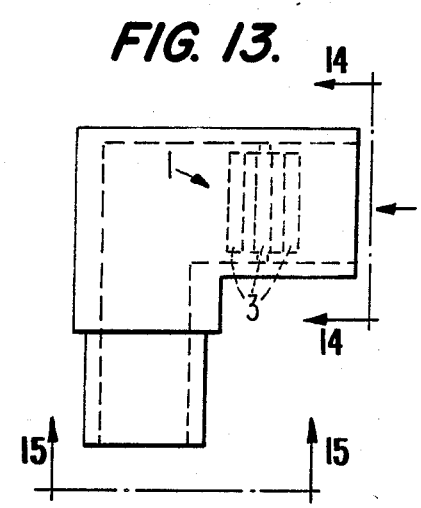

FIG. 13 depicts a system wherein monitor takes the form of a cylinder with openings and membranes (not shown) surrounding indicator compositions 3 on the interior and exterior circumference of the cylinder such that the gas atmosphere in the tube contacts the composition 3 on both sides of the cylindrical monitor 1.

Figure 14:
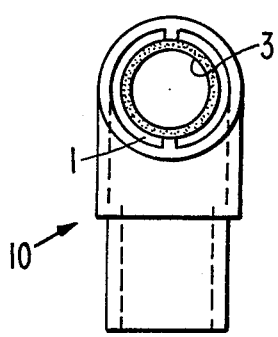
Figure 15:
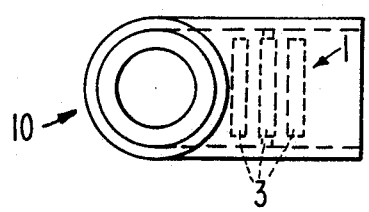

FIGS. 14 and 15 are views of the system from the ends of tube 10.

Figure 16:
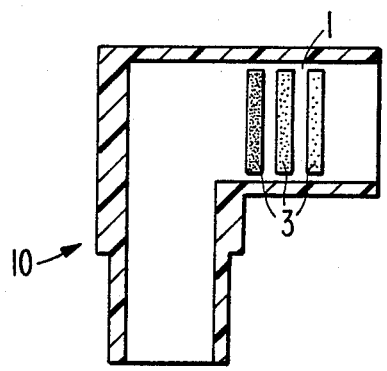

FIG. 16 is a cross-sectional, cut-away view of the system of FIG. 13 showing the three indicator compositions of varying degrees of sensitivity by different shadings.

The monitor of the invention and sytems embodying the monitor are far less expensive, more advantageous and easier to employ than those currently in use.

The design of the monitor allows it to be incorporated in existing connectors used in breathing circuits. Therefore, no additional component that might contribute to increased bulk, dead space, flow resistance or weight has to be inserted in the breathing circuit. In applications where space and weight considerations are important, (e.g., helicopter and airplane ambulances, space shuttle), the monitor would be more suitable than a bulky and heavy capnograph.

The monitor of the invention does not require a power supply to function.

The present invention does not require additional manipulations by the operator, merely a visual observation of the indicator, thereby freeing the operator for closer attention to the patient. Furthermore, the membrane in the monitor prevents escape of the indicator solution into the environment and the patient's system.

False readings are virtually impossible with the system and method of the invention since at least two indicators with different sensitivities to $CO_2$ are usually used. The more sensitive indicator will trigger with 1-4 exhaled breaths containing $CO_2$. The less sensitive indicator will respond within 5-9 exhaled breaths. The wide range in the number of exhaled breaths required to obtain a color change in the indicators is caused by the large variations in end-tidal $CO_2$ ($ETCO_2$) concentration, respiratory rate, tidal volume and exhalation flow patterns that can be expected in the patient population. During an esophageal intubation, any $CO_2$ trapped in the stomach will be completely washed out with 2-4 breaths, the number of breaths' required depending on the initial $CO_2$ level in the stomach, the size and degree of distension of the stomach and the tidal volume. Therefore, the less sensitive indicator will not trigger in these special cases and will serve to alert the operator.

The systems and method of the invention can be varied considerably depending upon the intended use, each having its advantages and drawbacks. The design features common to all variants are as follows:

(i) Chemical indicator solutions are used to detect $CO_2$. Any indicator that has a narrow range of pH (above 3.8, the pH of carbonic acid) in which it changes color is suitable. A narrow pH range for the required color change provides faster color change for a given $ETCO_2$.

(ii) The chemical indicators should not be harmful if aspirated in the lungs or stomach.

(iii) The change in color should be conspicuous and unequivocal; e.g., red to orange would not be acceptable.

(iv) The indicator should not give any color change with oxygen, nitrous oxide, and the commonly used volatile anesthetics (isoflurane, halothane, enflurane).

(v) The indicators are separated from the airway by a $CO_2$-permeable membrane made of silicone rubber (General Electric silicone polycarbonate copolymer—GE MEM-213, General Electric one-thousandth of an inch thick dimethyl silicone—GE 1 mil DMS, Dow Corning Silastic). The $CO_2$-permeable membrane allows $CO_2$ to permeate into the indicator while preventing the indicator from getting into the lungs.

The permeability rate of $CO_2$ across the membrane is governed by the equation [Robb, Report No. 65-C-031, General Electric Research and Development Center, Schenectady, NY, Oct. 1965]:

$$Q = (Pr \times DP \times A)/T$$

where

Q is the flowrate of $CO_2$ across the membrane (cc at STP/second)

Pr is the gas permeability which is constant for a given material and a specific gas (cc gas at STP. cm/sec. sq cm. cm Hg). For $CO_2$ in dimethyl silicone rubber, Pr is $270 \times 10^{-9}$. For $CO_2$ in GE MEM-213 membrane, Pr is $97 \times 10^{-9}$ [Gen. Elec. Membrane Products Operation Medical Systems Business Operations. Gen. Elec. Permselective Membranes, p. 10].

DP is pressure differential across the membrane (cm Hg).

A is the surface area of membrane exposed to $CO_2$ (square cm).

T is the membrane thickness (cm).

The permeability of the $CO_2$ membrane may be maximized by optimizing the parameters (decreasing membrane thickness, increasing surface area of the membrane and pressure differential across the membrane) that affect its permeability to $CO_2$.

As little indicator as possible should be used so that the amount of $CO_2$ molecules, and hence the time, required for an unequivocal color change is decreased.

The indicator is preferably disposed as a thin layer so that the surface area to volume ratio of the indicator is maximized.

A thin, chemically inert substrate, e.g., a white mesh fabric, may be placed in the thin layer of indicator to accentuate the color change by giving more "body" to the colors. A thin layer of indicator solution only is translucent and the colors are subdued. A thick layer of indicator will have a more pronounced color but will also take longer to change color.

The mesh also maintains a film of uniform thickness irrespective of the orientation of the connector by preventing pooling of the indicator solution towards the bottom part of the film. This is a desirable feature since during tests it was found that thicker films caused by pooling take longer to change color compared to thinner films. The mesh makes the response time of the indicator independent of the position of the connector.

Indicators with different sensitivities to $CO_2$ can preferably be used. Any number of indicators with different sensitivities to $CO_2$ can be used. The preferred minimal configuration is two indicators. The more sensitive indicator will typically change color with exposure to 1-4 breaths containing $CO_2$ while the less sensitive indicator will respond with 5-9 breaths. In the event of esophageal intubation and $CO_2$ somehow being present in the stomach, all the $CO_2$ will be washed out of the stomach within 2-4 breaths; the less sensitive indicator will not change color and will alert the operator. Three different indicators staged to respond at 1, 4 and 9 breaths should give the optimal coverage since the $CO_2$ sensitivity of each indicator can then be targeted at a narrower range of $CO_2$ exposure.

The less sensitive indicator can be obtained in many ways. Bench tests were conducted to investigate the effect of specific parameters (membrane thickness, membrane material, volume of indicator, pH of indicator and position of indicator on the connector) on the response time of the monitor at various $CO_2$ concentrations. Clearly, the type of indicator will also affect response time but this was not investigated in the tests described below. The tests consisted of passing 8 L/min of given $CO_2$ concentrations (1.0%, 2.1%, 4.8% and 9.2% measured by a capnograph) in dry oxygen past different elbow connectors and measuring the response time (time taken for an unequivocal color change from blue to yellow) for various combinations of parameters. Since large volumes of indicator were used (15 and 25 microLiters), the indicator film was thick. Therefore, the color of the indicator did not need enhancement and no mesh was used in the bench tests. Each test was performed three times.

Figure 17:
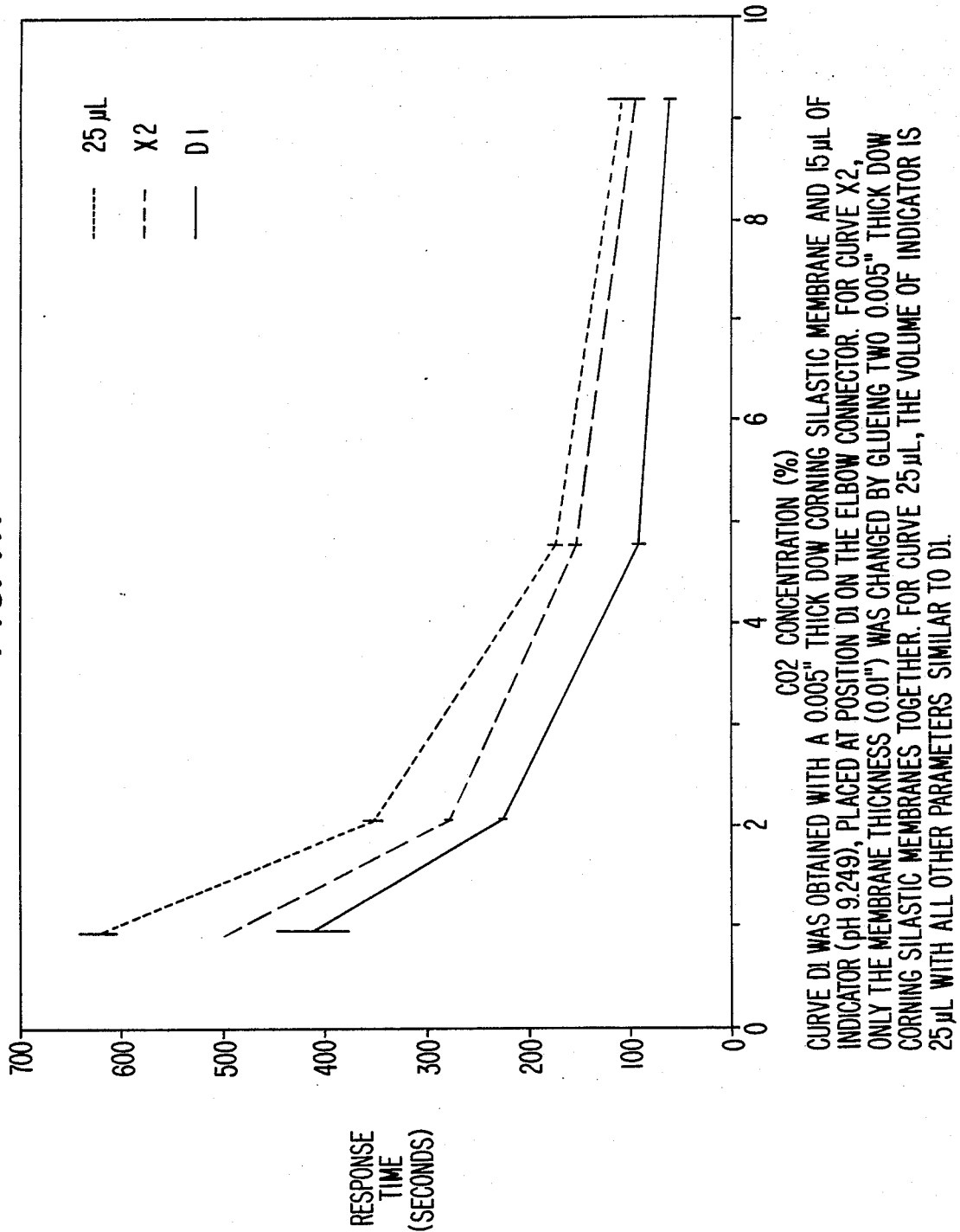
FIGS. 17–20 are graphical depictions of various of the results of the examples described herein.
Figure 18:
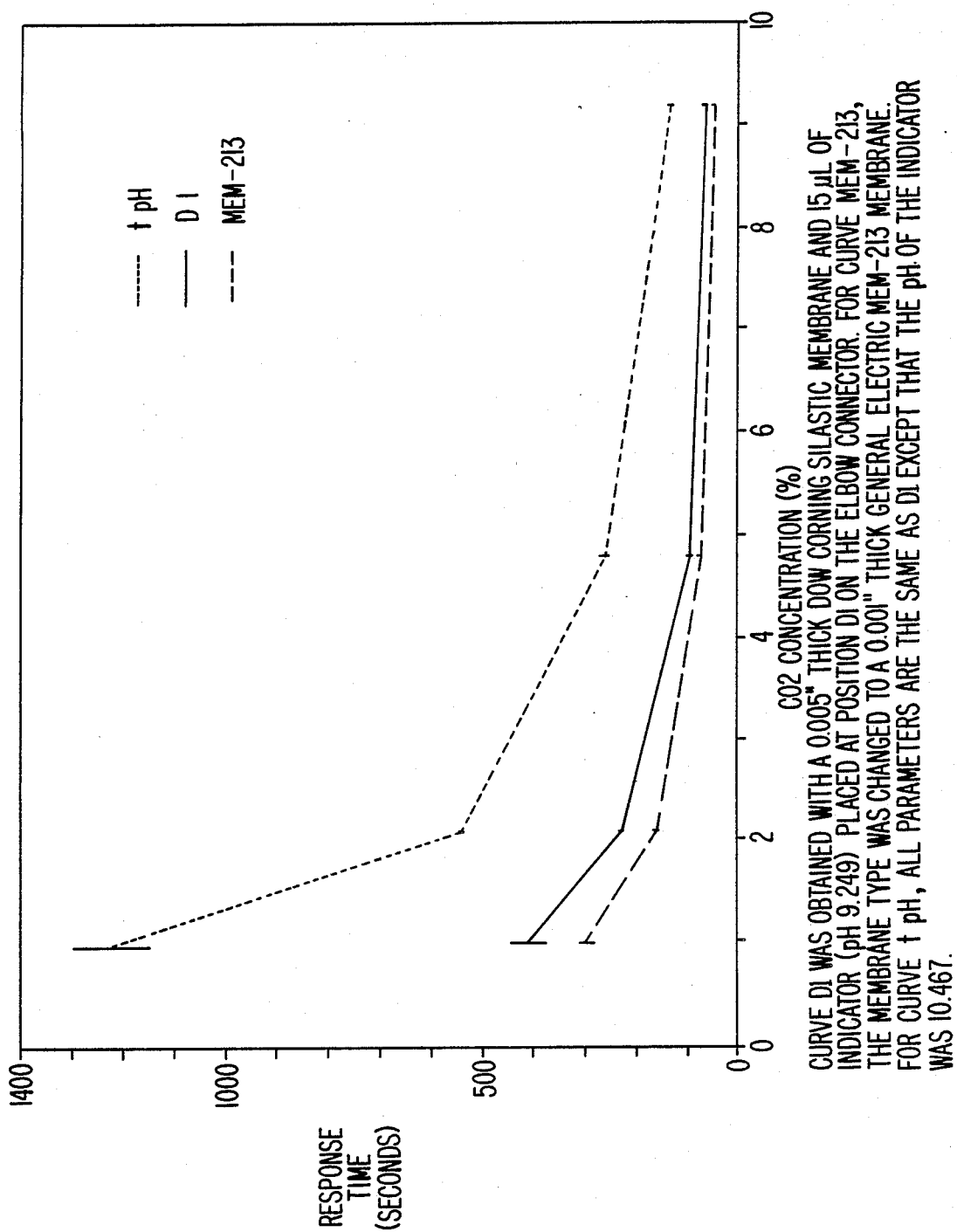

A thicker $CO_2$-permeable membrane or a larger volume of indicator slowed the response time at all $CO_2$ concentrations (FIG. 17). The type of $CO_2$-permeable membrane used, as well as the pH of the indicator, will also affect the response time (FIG. 18). Finally, the effect of geometry for a given connector was investigated. Theoretically, if the indicator is placed at a spot where the boundary layer is well developed, the effective permeability rate of the membrane configuration will be reduced [Robb, supra] resulting in a degradation of the response time. The boundary layer is a slow-moving layer of gas next to the surface of the membrane that slows the rate at which $CO_2$ molecules can permeate into the indicator since the molecules have to go through an additional "layer" before reaching the indicator. The boundary layer develops (becomes thicker) in the direction of the flow as long as there is no sharp angle on the surface along which the boundary layer is developing. From FIG. 3, it can be seen that during exhalation the boundary layer will be more developed at U1 than at D1 since there is a length of tubing without sharp angles (the endotracheal tube) upstream of U1 during exhalation, along which the boundary layer can develop. At D1, the exhaled flow impinges directly on the membrane and disrupts any boundary layer that may be developing.

Figure 19:
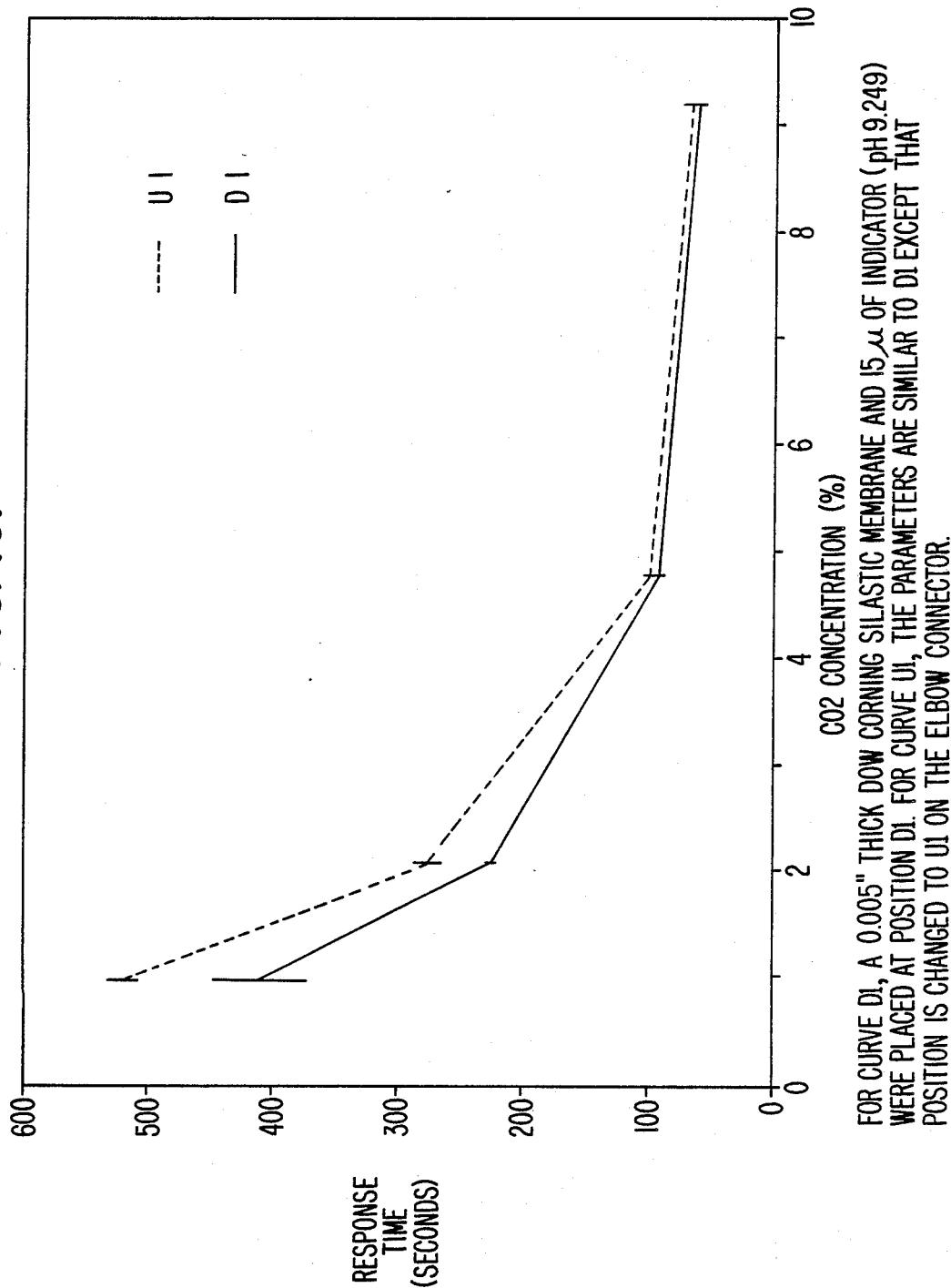

Position U1 was compared to position D1 on the elbow connector. There was no noticeable difference in response time between the two positions at $CO_2$ concentrations exceeding 5%; however, D1 was faster than U1 at $CO_2$ concentrations below 5% (FIG. 19).

In the prototypes used, reduced sensitivity to $CO_2$ was obtained by increasing the pH of the indicator by addition of 0.1 N NaOH. It is obvious from the results described above that the response time could be lengthened by increasing membrane thickness, changing the type of indicator, increasing the indicator film thickness or using a membrane material with a lower permeability rate to $CO_2$.

It is a desirable feature that all indicators change to the same color (yellow in the prototypes) which provides for an easy to remember interpretation.

The less sensitive indicator, if obtained by buffering the more sensitive indicator to a higher pH, will revert from yellow to royal blue if, for some reason, $CO_2$ stops being present in the exhaled gas. Therefore, the monitor can also give a qualitative measure of adequacy of ventilation and act as a guard against accidental movement of the ET tube during manipulation of the patient.

The device should not add bulk, weight or deadspace to the breathing circuit. Ideally, an existing component of the breathing circuit should be used. The technique should not require any additional tasks of the operator since during intubation there is already a multitude of urgent tasks to do.

The $CO_2$-permeable membrane is also permeable to solvent and will typically allow the indicator solution to dry out in 2-3 hours. The indicator will not work when dessicated. Therefore, the indicator is preferably wrapped in a solvent-impermeable plastic, e.g., high density polyethylene to prevent dessication. Prior to use, the solvent-impermeable wrapper is simply removed.

Figure 21:
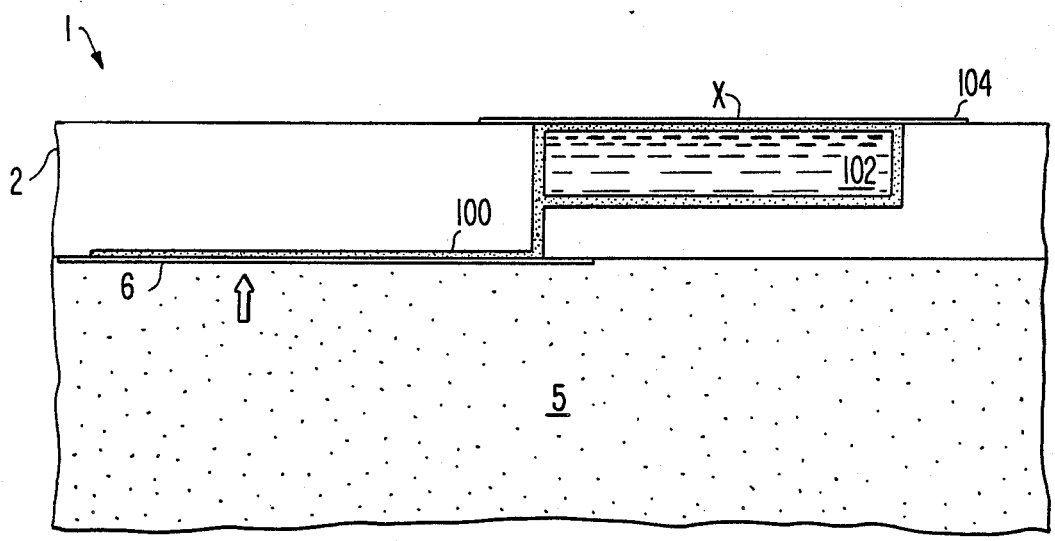
FIGS. 21–23 are side cross-sectional cut-away views of other embodiments of the $CO_2$ monitor of the invention.

Alternatively, as shown in FIG. 21, the indicator can be placed on the adapter as a dry powder on, e.g., chemically-inert blotting paper. On insertion of the monitor into the breathing circuit, solvent from a pouch or vial 102 is released by pushing on the plastic film 104 at area X to rupture the vial and makes contact with the blotting paper. Through capillary action, the solvent reaches the dry powder indicator to form a solution and is made ready for use.

The device should not introduce appreciable flow resistance in the breathing circuit so that the work of breathing is not significantly increased for spontaneously breathing patients.

Four specific designs are described in the following examples.

EXAMPLE 1

The presence of a developed boundary layer adjacent to the $CO_2$-permeable membrane degrades its permeability. The boundary layer can have the same effect as if the membrane thickness had been doubled, i.e., halve the permeability rate and consequently double the response time [Robb, supra]. On rounding a sharp bend, e.g., a 90 degree elbow, the boundary layer is disrupted and there is a local buildup of pressure, both factors tending to enhance the permeability. There is an elbow adapter used in most breathing circuits whose geometry can be exploited by placing the indicators as shown in FIG. 3.

EXAMPLE 2

In the first design, $CO_2$ can permeate into the indicator layer from one side only. However, a fin design as in FIG. 6 doubles the membrane area by placing $CO_2$-permeable membrane on each side of the indicator layer and allowing the $CO_2$ to permeate into the indicator from both sides (see FIGS. 1 and 2 for the details of a one-membrane and a two-membrane indicator).

EXAMPLE 3

A drawback of the first two designs is that the indicator pockets have to be looked at directly and are not visible from all viewing angles. The placement of bands of indicator on the elbow adapter as in FIG. 9 allows viewing at any angle, at the expense of slower response time.

EXAMPLE 4

The design in FIG. 13 allows viewing of the indicators from any angle, while still allowing $CO_2$ to permeate into the indicator layer from both sides. The indicator bands are placed on a cylinder that is concentric to the bore of the elbow adapter.

Figure 22:
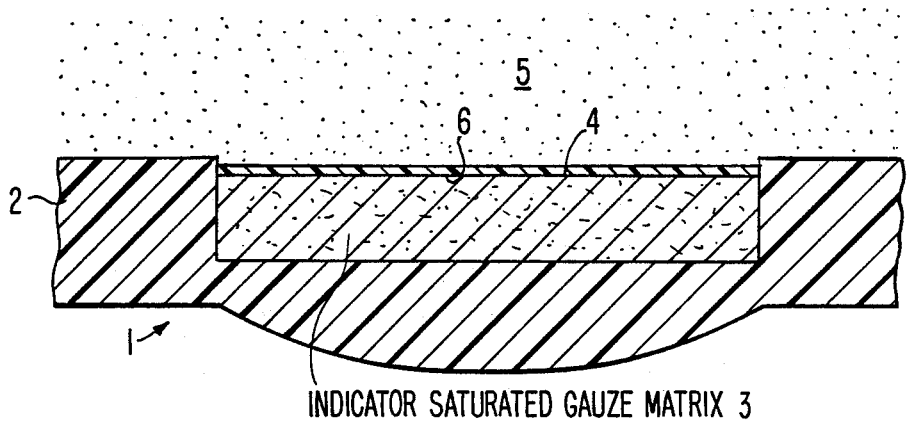
Figure 23:
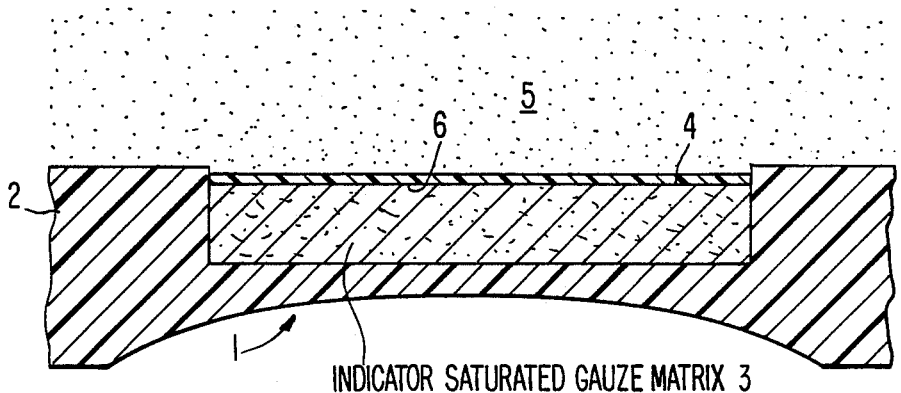

Obviously, many possible equivalent variants of the concept of the invention will occur to those skilled in the art. For example, vortex shedders can be placed on the bore of the adapter which will disrupt the boundary layer. The indicator enclosed in a $CO_2$-permeable membrane concept can be applied to any connector (elbow, straight, Y-piece, T-piece, ET tube adapter, etc.) used in a breathing circuit or to the endotracheal tube itself. For connectors that are manufactured with transparent plastic, the mold can be altered so that a lens is positioned over the indicator; the lens can be designed to either magnify the size of a small dot of indicator or intensify the color of the indicator. Such systems are shown in FIGS. 22 and 23 which show, respectively, a convex lens arrangement for size magnification and a concave lens for color intensification.

EXAMPLE 5

The solvent-impermeable wrapper is removed from the monitor having these indicators described above which is then placed at the patient end of the breathing circuit. After intubation, the monitor is attached to the ET tube. Four outcomes are now possible:

(1) If after 4 breaths, the more sensitive indicator has not changed color, the patient is extubated and mask-ventilated while the monitor is replaced with a fresh one and then another attempt is made at intubation.

(2) If the more sensitive indicator changes color within 4 breaths but the slower indicator does not change color within 9 breaths, then esophageal intubation with $CO_2$ in the stomach is a strong possibility. The patient is extubated and mask-ventilated while the monitor is replaced with a fresh one and then another attempt is made at intubation.

(3) If all the indicators change color within 9 breaths, the adapter is left in place.

(4) If during the procedure, the color of the less sensitive indicator reverts to its original color, the operator should be highly suspicious that the ET tube has slipped out of the trachea or that the patient is no longer being ventilated. The operator should then check the ET tube and see if the pilot balloon is properly inflated or otherwise reassess placement of the endotracheal tube and delivery of tidal volume.

EXAMPLE 6

Prototypes of the design described in Example 1 were built and tested. For the prototypes, a solution 0.1% bromothymol blue and 0.1% phenolphthalein in ethanol was buffered with 0.001 N NaOH to a pH of 9.249 for the most sensitive indicator. The color change with exposure to $CO_2$ is from ink-blue to bright yellow. The sensitivity of the indicator to $CO_2$ can be reduced by increasing pH through addition of base solution. Three indicators with reduced sensitivities to $CO_2$ (pH of 9.772, 10.189 and 10.467) were thus obtained from the stock indicator by addition of 0.1 N NaOH. For the slower indicators, the color change with exposure to $CO_2$ was royal blue to bright yellow.

The sensitivity of the "stock" indicator solution (pH 9.249) to oxygen, nitrous oxide and volatile anesthetics was tested using the monitor of Example 1 with a GE 1-mil DMS membrane, attached to a circle system breathing circuit. The test consisted of ventilating a bag at a respiratory rate of 10 bpm, a minute volume of 7 L/min, a fresh gas flowrate of 5 L/min and an I:E ratio of 1:2 with different gas mixtures for 5 minutes for each gas mixture. The mixtures used were:

a) 3.5 L/min N20, 1.5 L/min O2, no volatile anesthetics.
b) 3.5 L/min N2O, 1.5 L/min O2, 5% halothane
c) 3.5 L/min N2O, 1.5 L/min O2, 1% halothane
d) 3.5 L/min N2O, 1.5 L/min O2, 5% forane
e) 3.5 L/min N2O, 1.5 L/min O2, 1% forane
f) 3.5 L/min N2O, 1.5 L/min O2, 7% enflurane
g) 3.5 L/min N2O, 1.5 L/min O2, 2% enflurane.

No color change of the "stock" indicator (4 microLiters with no mesh) was obtained with any of the gas mixtures. Stock phenol red solution was also tested as a possible indicator. Phenol red was tested with gas mixtures, a, b, d, f only. No color change was obtained with these mixtures.

EXAMPLE 7

The monitor was tested on a goat which was esophageally intubated. A monitor of Example 1 with a GE 1-mil DMS membrane and 2 microLiters of stock indicator spread on a piece of mesh was connected into the breathing circuit. The goat was ventilated for 80 seconds with no color change of the indicator.

EXAMPLE 8

Figure 20:
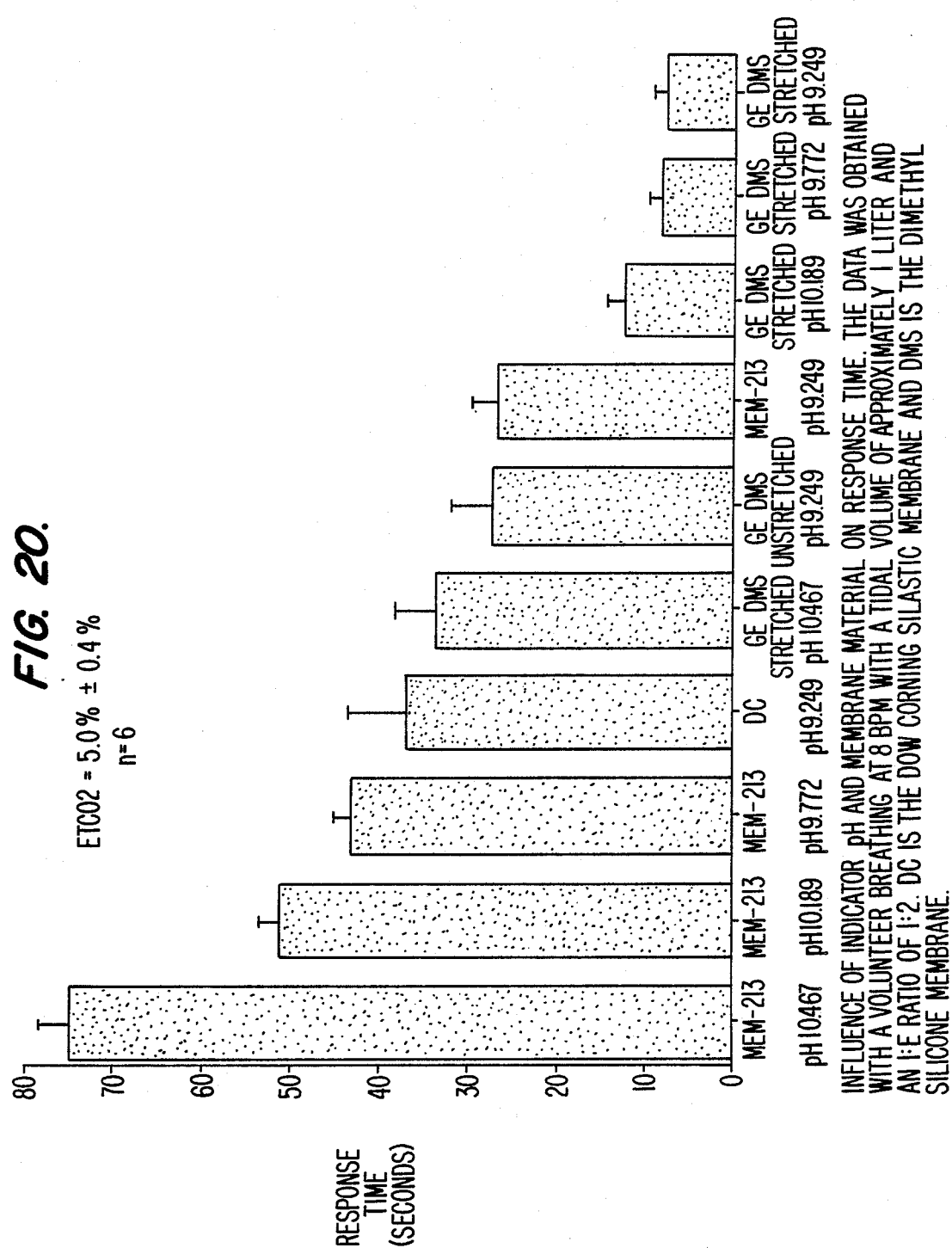

The data in FIG. 20 were obtained from a volunteer breathing air on a simulated circle system at a rate of 8 breaths/min with a tidal volume of approximately 1 liter, at an I:E ratio of 1:2. In all these tests, the end-tidal $CO_2$ concentration measured with a capnograph was 5.0% with a variation of 0.4%. The volume of indicator used was approximately 2 microLiters and a piece of mesh was always used. Each test was performed 6 times. The influence of pH and membrane type on response time is clearly evident.

We claim:

1. A self-contained diagnostic monitor for screening the $CO_2$ content of a gas exiting a patient during endotracheal or esophageal intubation comprising: (1) a reservoir containing at least one portion of a composition having an initial pH in solution above about 3.8 and which substantially changes color in solution in response to exposure to $CO_2$, said reservoir having an opening adapted for communication only with said gas exiting and entering said patient during endotracheal or esophageal intubation; and (2) a semipermeable membrane which is permeable to $CO_2$, said membrane separating said at least one composition portion from said exiting and entering gases, and wherein said reservoir contains a plurality of composition portions having initial pH is solution above about 3.8 and which substantially change color in solution in response to exposure to $CO_2$, and further comprising a plurality of semi-permeable membranes having differing thicknesses and/or $CO_2$ permeabilities and/or surface areas, each semipermeable membrane separating a corresponding composition portion from said exiting and said entering gas, and each one of said plurality of composition portions separated from every other composition portion by at least one semi-permeable membrane, and each of said plurality of composition portions requiring a different time of exposure to $CO_2$ to effect said change in pH thereby causing said color change.

2. The monitor of claim 1 wherein said reservoir is constructed substantially of a substantially transparent material for exteriorly viewing said color change in said at least one composition.

3. The monitor of claim 1 wherein said composition contains a solid inert substrate having a construction which enhances the viewing of said color change and maintains the dimensions of said at least one composition substantially constant irrespective of the orientation of said reservoir.

4. The monitor of claim 1 wherein each of said plurality of compositions has a different initial pH.

5. The monitor of claim 1 wherein each of said plurality of compositions is separated from said exiting gas by semipermeable membranes having differing thicknesses and/or $CO_2$ permeabilities and/or surface areas.

6. The monitor of claim 1 wherein said at least one composition is a liquid and said monitor is sealed in a fluid tight, removable wrapper to prevent dessication of said at least one composition prior to use thereof in said intubation.

7. The monitor of claim 1 wherein said at least one composition is non-liquid and said reservoir contains means for holding a liquid solvent separate from said dry composition and for introducing the liquid solvent to said composition prior to or during said intubation.

8. The monitor of claim 1 having a magnifying or condensing lens positioned thereon to enhance viewing of said color change.

9. The monitor of claim 1 wherein said at least one composition is a buffered solution of bromothymol blue and phenolphthalein.

10. In an endotracheal or esophageal intubation system containing means through which gases exit the patient during said intubation, the improvement comprising a self-contained diagnostic monitor for screening the $CO_2$ content of a gas exiting said patient during said intubation comprising: (1) a reservoir containing at least one portion of a composition having an initial pH in solution above about 3.8 and which substantially changes color in solution in response to exposure to $CO_2$, said reservoir having an opening adapted for communication only with said gases exiting and entering during said intubation; and (2) a semipermeable membrane which is permeable to $CO_2$, said membrane separating said at least one composition portion from said exiting and entering gases, and wherein said reservoir contains a plurality of composition portions having initial pH in solution above about 3.8 and which substantially change color in solution in response to exposure to $CO_2$, and further comprising a plurality of semipermeable membranes having differing thicknesses and/or $CO_2$ permeabilities and/or surface areas, each semipermeable membrane separating a corresponding composition portion from said exiting and said entering gas, and each one of said plurality of composition portions separated from every other composition portion by at least one semi-permeable membrane, and each of said plurality of composition portions requiring a different time of exposure to $CO_2$ to effect said change in pH thereby causing said color change.

11. The system of claim 10 wherein said reservoir is constructed substantially of a substantially transparent material for exteriorly viewing said color change in said at least one composition.

12. The system of claim 10 wherein said composition contains a solid inert substrate having a construction which enhances the viewing of said color change and maintains the dimensions of said at least one composition substantially constant irrespective of the orientation of said reservoir.

13. The sytem of claim 10 wherein each of said plurality of compositions has a different initial pH.

14. The system of claim 10 wherein each of said plurality of compositions is separated from said exiting gases by semipermeable membranes having differing thicknesses and/or $CO_2$ permeabilities and/or surface areas.

15. The system of claim 10 wherein said at least one composition is a liquid and said monitor is sealed in a fluid tight, removable wrapper to prevent dessication of said at least one composition prior to use thereof in said intubation.

16. The system of claim 10 wherein said at least one composition is non-liquid and said reservoir contains means for introducing a liquid solvent to said composition prior to or during said intubation.

17. The system of claim 10 having a magnifying or condensing lens positioned thereon to enhance viewing of said color change.

18. The monitor of claim 10 wherein said at least one composition is a buffered solution of bromothymol blue and phenolphthalein.

19. The system of claim 11 wherein said means through which said gases exit said patient is an elongated esophageal cannula having a distal end adapted for insertion into the esophagus of said patient, said opening in said reservoir of said monitor communicating with said exiting gases via an opening in the proximal end of said cannula.

20. The system of claim 19 wherein said respective openings in said reservoir and said proximal end of said cannula form a seal which is substantially fluid tight with respect to the ambient temperature.

21. In a method for monitoring the $CO_2$ content of gases exiting a patient during endotracheal or esophageal intubation, the improvement comprising providing a self-contained $CO_2$ diagnostic monitor and contacting said exiting gases with said monitor, the monitor having a reservoir containing a plurality of composition portions having an initial pH solution above about 3.8 and which substantially changes color in solution in response to $CO_2$, said reservoir having an opening adapted for communication only with said entering and exiting gases during said intubation, each composition portion separated from other composition portions and each composition portion requiring a different time of exposure to $CO_2$ to effect said change in pH thereby causing said color change; a plurality of semipermeable membranes having differing thicknesses and/or $CO_2$ permeabilities and/or surface areas, each semi-permeable membrane permeable to $CO_2$ and separating a corresponding one of said composition portions from said entering and exiting gases; and viewing said plurality of composition portions.

22. The method of claim 21 wherein said reservoir is constructed substantially of a substantially transparent material for exteriorly viewing said color change in said at least one composition.

23. The method of claim 21 wherein said composition contains a solid inert substrate having a construction which enhances the viewing of said color change and maintains the dimensions of said at least one composition substantially constant irrespective of the orientation of said reservoir.

24. The method of claim 21 wherein each of said plurality of compositions has different initial pH.

25. The method of claim 21 wherein each of said plurality of compositions is separated from said exiting gases by semipermeable membranes having different thicknesses and/or $CO_2$ permeabilities and/or surface areas.

26. The method of claim 21 wherein said at least one composition is a liquid and said monitor is sealed in a fluid tight, removable wrapper to prevent dessication of said at least one composition prior to use thereof in said intubation.

27. The method of claim 21 wherein said at least one composition is non-liquid and said reservoir contains means for introducing a liquid solvent to said composition prior to or during said intubation.

28. The method of claim 21 having a magnifying or condensing lens positioned thereon to enhance viewing of said color change.

29. The method of claim 21 wherein said at least one composition is a buffered solution of bromothymol blue and phenolphthalein.

30. In an endotracheal intubation system containing means through which gases exit the patient during said intubation, the improvement comprising a self-contained diagnostic monitor for screening the $CO_2$ content of a gas exiting said patient during said intubation comprising: (1) a reservoir containing at least one portion of a composition having an initial pH in solution above about 3.8 and which substantially changes color in solution in response to exposure to $CO_2$, said reservoir having an opening adapted for communication only with said gases exiting and entering during said intubation; and (2) a semipermeable membrane which is permeable to $CO_2$, said membrane separating said at least one composition from said exiting and entering gases, said system further comprising an endotracheal tube, and wherein said monitor is a part of the endotracheal tube and wherein said reservoir contains a plurality of composition portions having an initial pH in solution above about 3.8 and which substantially change color in solution in response to exposure to $CO_2$ and further comprising a plurality of semi-permeable membranes having differing thicknesses and/or $CO_2$ permeabilities and/or surface areas, each semi-permeable membrane separating a corresponding composition portion from said exiting and said entering gas, and each one of said plurality of composition portions separated from every other compositions portion by at least one semi-permeable membrane, and each of said plurality of composition portions requiring a different time of exposure to $CO_2$ to effect said change in pH thereby causing said color change.

* * * * *

UNITED STATES PATENT AND TRADEMARK OFFICE
CERTIFICATE OF CORRECTION

PATENT NO. : 4,928,687

DATED : May 29, 1990

INVENTOR(S) : LAMPOTANG, ET AL

It is certified that error appears in the above-identified patent and that said Letters Patent is hereby corrected as shown below:

Column 13, line 15:

In line 15 of claim 1, delete "is" and insert -- in --

Signed and Sealed this

Fifteenth Day of October, 1991

*Attest:*

*Attesting Officer*

HARRY F. MANBECK, JR.

*Commissioner of Patents and Trademarks*